(12) United States Patent
Kennedy

(10) Patent No.: US 8,256,424 B2
(45) Date of Patent: Sep. 4, 2012

(54) FERTILITY REGULATOR INCORPORATING VAS DEFERENS IMPLANTED OPEN/CLOSE BYPASS IN COMBINATION WITH A HAND HELD CONTROLLER FOR WIRELESS POWER TRANSFER

(76) Inventor: Patrick J. Kennedy, Belleville, MI (US)

( * ) Notice: Subject to any disclaimer, the term of this patent is extended or adjusted under 35 U.S.C. 154(b) by 0 days.

(21) Appl. No.: 12/887,658

(22) Filed: Sep. 22, 2010

(65) Prior Publication Data

US 2011/0067705 A1    Mar. 24, 2011

Related U.S. Application Data

(60) Provisional application No. 61/244,629, filed on Sep. 22, 2009.

(51) Int. Cl.
*A61F 6/02* (2006.01)
*A61B 5/05* (2006.01)
*A61B 17/08* (2006.01)
(52) U.S. Cl. ............... 128/843; 600/419; 606/158
(58) Field of Classification Search ............... 600/459, 600/417, 425, 437, 439, 462, 461, 463, 467; 606/158, 157, 151, 1; 128/842, 843
See application file for complete search history.

(56) References Cited

U.S. PATENT DOCUMENTS

| | | | |
|---|---|---|---|
| 3,589,355 A | 6/1971 | Lee | |
| 3,699,957 A * | 10/1972 | Robinson | 128/843 |
| 3,731,670 A * | 5/1973 | Loe | 600/30 |
| 3,990,434 A | 11/1976 | Free | |
| 4,200,088 A | 4/1980 | Denniston, Jr. | |
| 4,245,638 A | 1/1981 | Lebeck et al. | |
| 4,269,174 A | 5/1981 | Adair | |
| 4,512,342 A | 4/1985 | Zaneveld et al. | |
| 4,682,592 A | 7/1987 | Thorsgard | |
| 4,788,966 A | 12/1988 | Yoon | |
| 5,065,751 A | 11/1991 | Wolf | |
| 5,471,997 A | 12/1995 | Thompson | |
| 5,795,288 A | 8/1998 | Cohen et al. | |
| 5,935,137 A | 8/1999 | Saadat et al. | |
| 6,090,063 A | 7/2000 | Makower et al. | |
| 6,852,082 B2 | 2/2005 | Strickberger et al. | |
| 2009/0131959 A1 * | 5/2009 | Rolland | 606/158 |
| 2009/0247817 A1 * | 10/2009 | Forsell | 600/31 |
| 2009/0254106 A1 * | 10/2009 | Forsell | 606/157 |

* cited by examiner

*Primary Examiner* — Patricia Bianco
*Assistant Examiner* — Tarla Patel
(74) *Attorney, Agent, or Firm* — Gifford, Krass, Sprinkle, Anderson & Citkowski, P.C.

(57) ABSTRACT

An on/off fertility regulator device in the form of a male vas deferens or female fallopian tube bypass mounted device incorporating an open/close valve actuator. A separate hand-held controller is positioned above the skin and in proximity to the previously implanted regulating device. Wireless energy transfer receiver circuitry is built into the device and, upon receiving a electric generated signal the inductive circuit printed coil activates the actuator in order to actuate any of a clamp, ball, globe or flow interrupter associated with a bypass connection tube associated with each of the pair of vas deferens. As a result, passage of semen from the seminal vesticle (or alternatively eggs through the fallopian tube) can be instantly interrupted or permitted in on/off fashion as a viable alternative to the user undergoing an irreversible vasectomy operation.

5 Claims, 5 Drawing Sheets

FIG. 7A
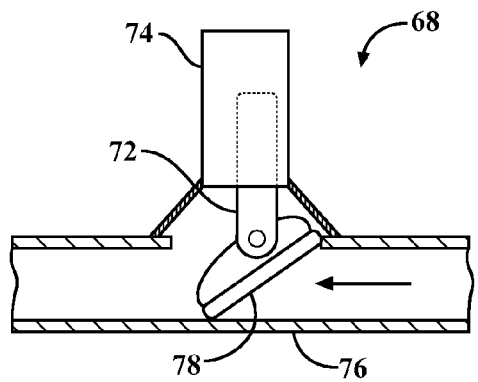
FIG. 7B
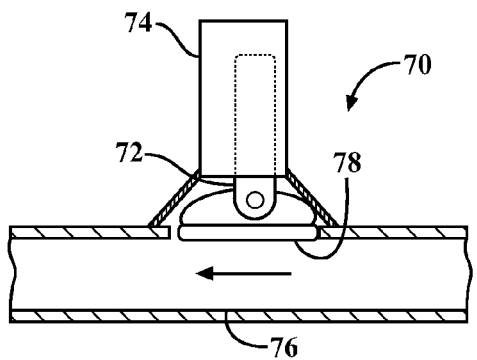
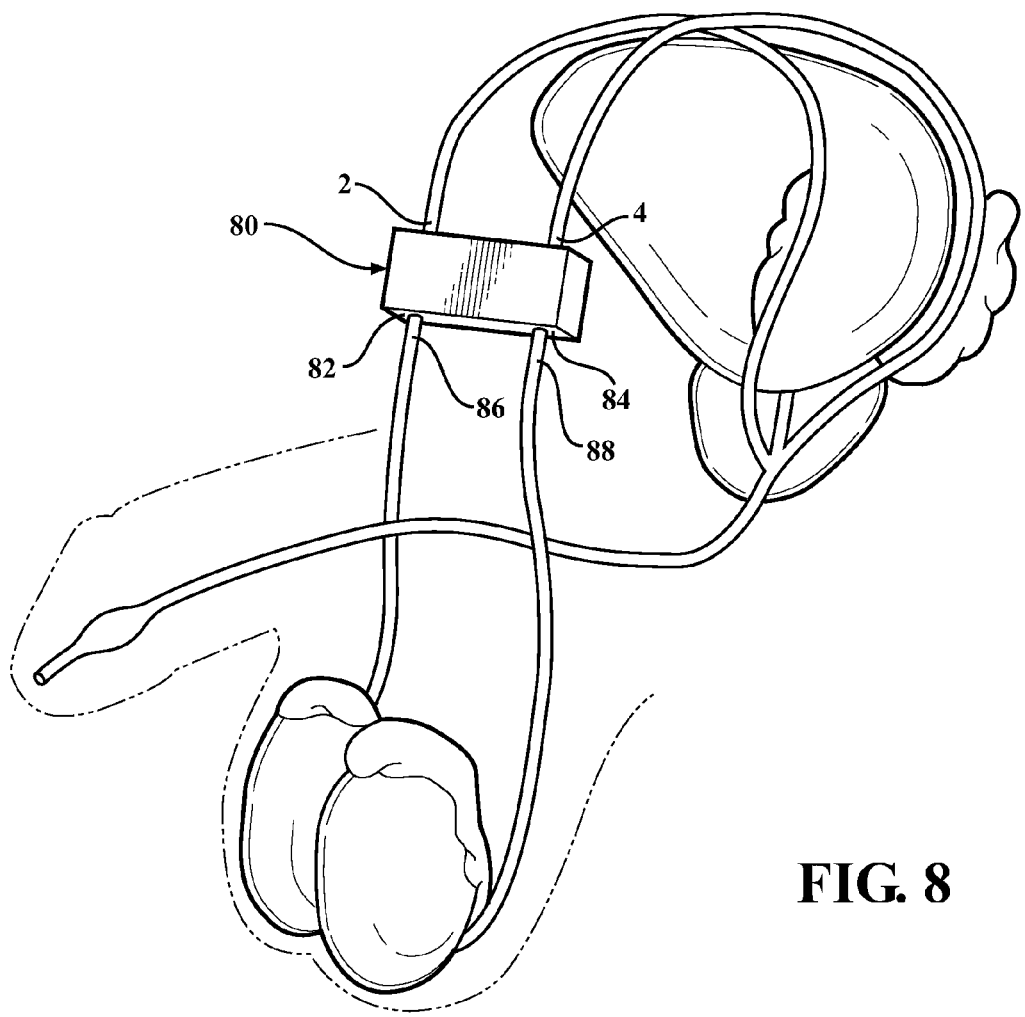
FIG. 8

FERTILITY REGULATOR INCORPORATING VAS DEFERENS IMPLANTED OPEN/CLOSE BYPASS IN COMBINATION WITH A HAND HELD CONTROLLER FOR WIRELESS POWER TRANSFER

CROSS-REFERENCE TO RELATED APPLICATIONS

This Application claims the benefit of U.S. Provisional Application 61/244,629 filed on Sep. 22, 2009.

FIELD OF THE INVENTION

The present invention relates generally to fertility regulation devices for male or female and, more specifically, discloses an on/off fertility regulator device in the form of a vas deferens bypass mounted device incorporating an open/close valve actuator. A separate handheld controller is positioned above the skin and in proximity to the previously implanted regulating device. Wireless energy transfer receiver circuitry is built into the device and, upon receiving an DC or AC generated signal the inductive circuit printed coil (or other device or method operating to receive the energy and signal transmission) activates the actuator in order to actuate any of a clamp, ball, globe or flow interrupter associated with a bypass connection tube associated with each of the pair of vas deferens with the result that passage of semen from the seminal vesicle can be instantly interrupted or permitted in on/off fashion and as a viable alternative to the user undergoing a vasectomy operation.

BACKGROUND OF THE INVENTION

The prior art is documented with varying types of fertility assist and regulation devices, nominal among these being U.S. Pat. No. 6,852,082 to Strickberger for use in combination with a tissue clamp for performing a non-invasive vasectomy. U.S. Pat. No. 5,065,751, to Wolf teaches a method and apparatus for reversibly occluding a biological tube. An occluding member exhibits an inner core and outer shell and is implanted in obstructing fashion within the biological tube (e.g. vas deferens). When it is desired to eliminate the obstruction, shock wave lithotripsy or other energy is employed to fragment the occluding member.

Without exception, the prior art in this technology teaches one form or another of a vas deferens implanted plug, balloon or like obstruction, with the shortcoming in each being failure to provide any type of on/off (or open/closed) positioning in an non-invasive fashion. Rather, it is presumed in each instance that a follow up removal operation would be desired in order to remove the implant.

SUMMARY OF THE INVENTION

The present invention relates generally to fertility regulation devices and, more specifically, discloses an on/off fertility regulator device in the form of a vas deferens bypass mounted device incorporating an open/close valve actuator. A separate handheld controller is positioned above the skin and in proximity to the previously implanted regulating device.

Wireless energy transfer receiver circuitry is built into the device and, upon receiving an AC generated signal the inductive circuit printed coil activates the actuator in order to actuate any of a clamp, ball, globe or flow interrupter associated with a bypass connection tube associated with each of the pair of vas deferens (or alternatively fallopian tubes). As a result, in the case of a male user the passage of semen from the seminal vesicle can be instantly interrupted or permitted in on/off fashion as a viable alternative to the user undergoing an irreversible vasectomy operation. In the case of a female user, an egg and semen may be instantly blocked, or permitted passage, in an on/off fashion.

An added feature of the invention is that the necessary power for actuating the once implantable device is further provided by the transmitter, thus avoiding the necessity of removing the implant such as to replace batteries. A related variant is also disclosed and which, in substitution of the vas deferens tubes, can be implanted in a female patient and in interrupting proximity to the fallopian tubes.

A further embodiment discloses a tubal bladder control assistance device which creates constriction around the urethra assisting the sphincter in preventing the bladder from premature release of stored urine. A manual release feature is provided by a hand held device for emptying at a desired time.

BRIEF DESCRIPTION OF THE DRAWINGS

Reference will now be made to the attached drawings, when read in combination with the following detailed description, wherein like reference numerals refer to like parts throughout the several views, and in which:

FIGS. 7A and 7B illustrate closed and open positions of an angled gate valve configuration;

FIG. 8 is an environmental illustration of one version of vas deferens interrupting implant mounted in accordance with the present invention;

DETAILED DESCRIPTION OF THE PREFERRED EMBODIMENTS

Figure 9:
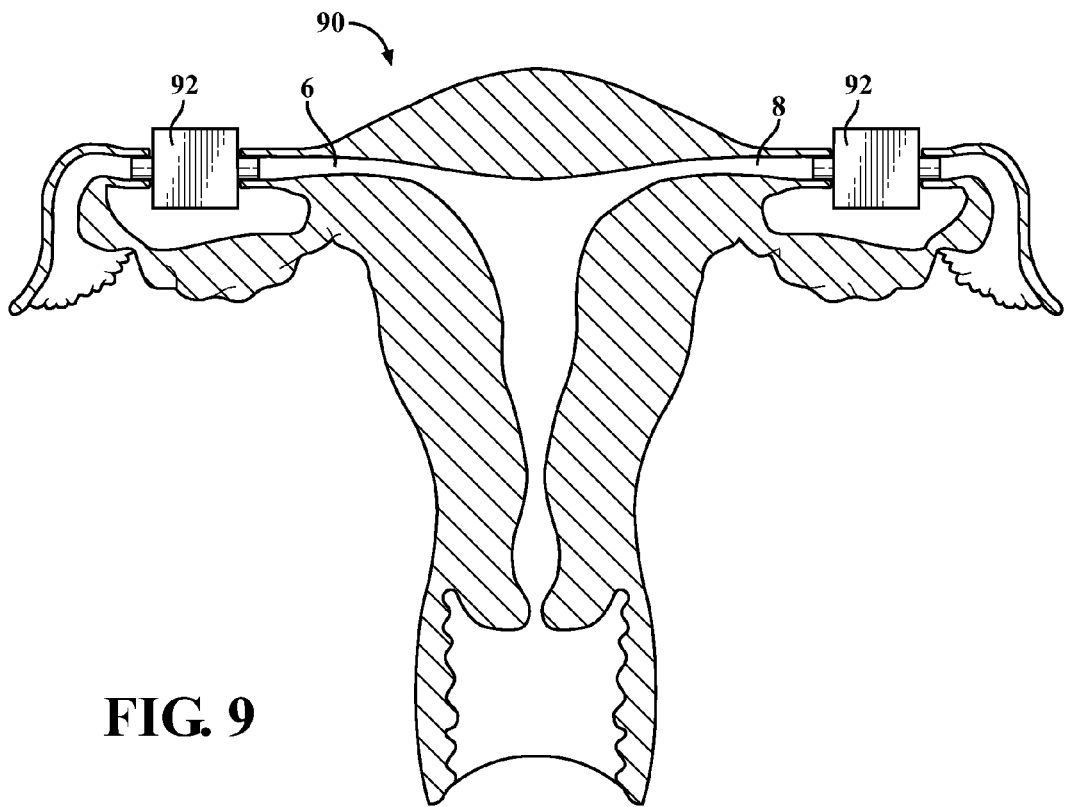
FIG. 9 is an illustration of a regulator device, such as previously described, and incorporated into either of the female fallopian tubes.

As previously described, the present invention describes a fertility regulator incorporating a first patient-implantable device and which provides an on/off bypass arrangement with either a male patient (vas deferens variant as depicted in FIG. 8) or a female patient (fallopian tube variant as depicted in FIG. 9). As will be further described in reference to successive embodiments, a separate handheld controller is positioned above the skin and in proximity to the previously implanted regulating device, such that wireless energy transfer receiver circuitry incorporated into the device causes such as an electromagnetic actuation (or like form of wireless energy transfer) of a valve element associated with the implanted device in order to selectively open or close the same in any repetitively desired fashion.

Figure 1:
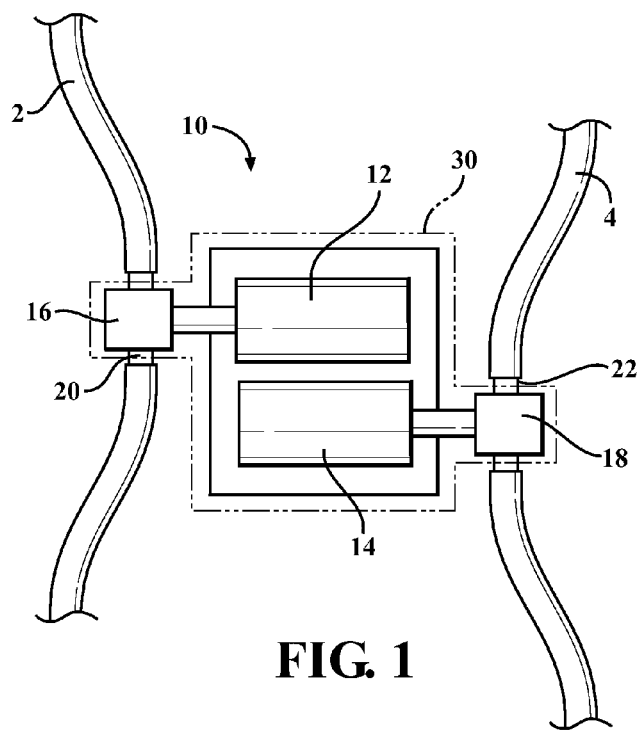
FIG. 1 is a part breakdown illustration of one variant of a fertility regulator, using dual actuators to actuate their respective seminal valve. The actuators would be activated by means of an externally positioned hand-held controller for providing an electromagnetic generating input (or like form of wireless energy transfer) to cause opening/closing of the actuator component.

Referring to FIG. 1, a part breakdown illustration is generally depicted by housing 10 of one variant of a fertility regulator, and which utilizes dual actuators 12 and 14 which actuate respective seminal valves further depicted at 16 and 18, respectively. The valves 16 and 18 are positioned so that they selectively interrupt conduit locations associated with first 2 and second 4 vas deferens locations in the case of a male implantation. As further depicted the vas deferens 2 and 4 can be sectioned at proximate locations at the time of implantation, with the sectioned ends being reattached to inter-fitting nipple portions (see further at 20 and 22 in FIG. 1).

Figure 11:
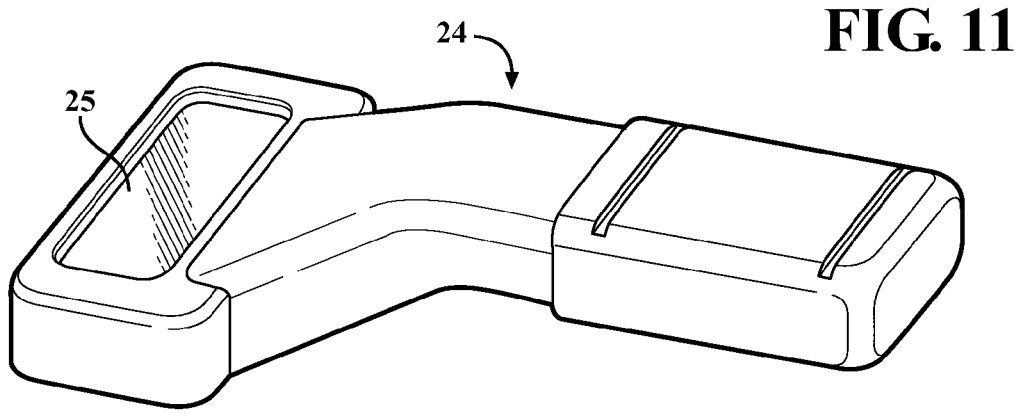
FIG. 11 is an illustration of the handheld device according to one variant of the invention.

Referring to FIG. 11, the actuators are activated (or otherwise triggered) by means of an externally positioned handheld controller 24 for providing an electromagnetic (or like form of wireless energy transfer) generating input to cause opening/closing of the actuator components. Wireless energy transfer receiver circuitry is incorporated into the body of device 10 (such as within its shell construction) and is configured in order to receive an electrical signal (e.g., a DC or alternatively AC signal) from a hand held controller 24 (see FIG. 11) which, upon receipt by the implanted device that includes an inductive circuit printed coil in order to actuate any of a clamp, ball, globe or flow interrupter associated with a bypass connection tube associated with each of the pair of vas deferens (and/or any of the other invention variants). In this fashion, the requirement for batteries is dispensed with in terms of the implanted device.

Figure 2:
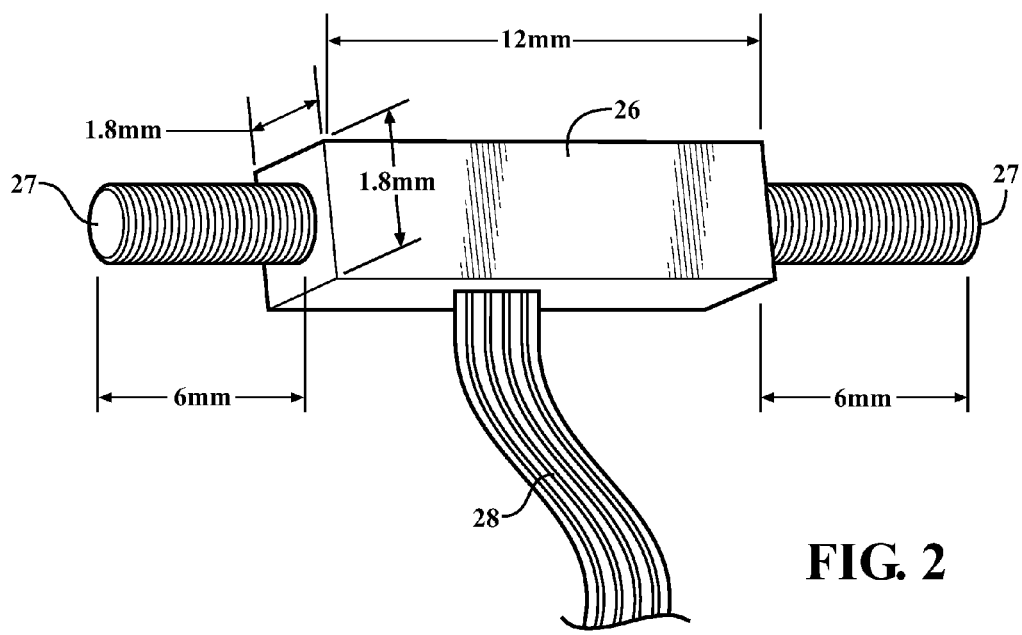
FIG. 2 is an example or an actuator component as may be incorporated into one variant of the invention, figuratively shown in FIG. 1.

As further depicted in FIG. 2, another variation of selected actuator 26 is shown which can be interposed within a selected sectioned location of vas deferens and can exhibit any specified shape and size (in one non-limiting variant including a 1.8 mm×1.8 mm×6 mm package dimension which further includes a 6 mm stroke using a 12 mm shaft upon which the valve components 16 and 18 are supported. A pair of actuators 26 (similar to the dual arrangement at 12 and 14 in FIG. 1) may be implanted in selectively blocking fashion within each a pair of reproductive ducts, such as vas deferens connection tubes again representatively illustrated at 2 and 4 (see also environmental view of FIG. 8). In this fashion, the entire unit with the exception of the spliced ends of the vas deferens tubes attachable to opposite nipple ends 27, is completely sealed. A conduit ribbon 28 is also illustrated and which can communicate an DC or like electromagnetic input (e.g., AC) in order to actuate the internal valve components (not shown) associated with the actuator 26.

The hand-held controller device 24 as again shown in FIG. 11 incorporates a wireless energy transmitter for creating a (DC or alternatively AC) signal which energizes the internal receiver 28 circuitry. Upon having previously implanted the fertility regulator in proximity to the patient's reproductive ducts (e.g., vas deferens), the external controller device (shown in FIG. 11) is positioned in proximity to the device (i.e. such as in close proximity to the exterior skin surface). The energy transmitter (e.g., DC or AC generated) component incorporated into the powered controller device (representatively illustrated at 25 in FIG. 11) causes energizing of such as a magnetic coil 30 (or similar component)(see as representatively illustrated in FIG. 1) associated with the implanted actuators 12 and 14, which causes them to simultaneously shift between open and closed positions.

In this fashion, the requirement for batteries within the fertility regulator is avoided, with all necessary power generation occurring at the hand-held controller (see again FIG. 11). That said, additional embodiments contemplate that the fertility regulator can be driven by an external power source generated within the hand held controller. This form of wireless power transfer such as induction, radio frequency or another variant of wireless power transfer would allow for the devise to be implanted and requiring no further invasion of the body. This device would contain no energized circuitry except during the extremely limited period where the valves are being switched between open and shut positions. These forms of power transfer are extremely safe due to the synchronization of resonant frequencies.

Figure 3:
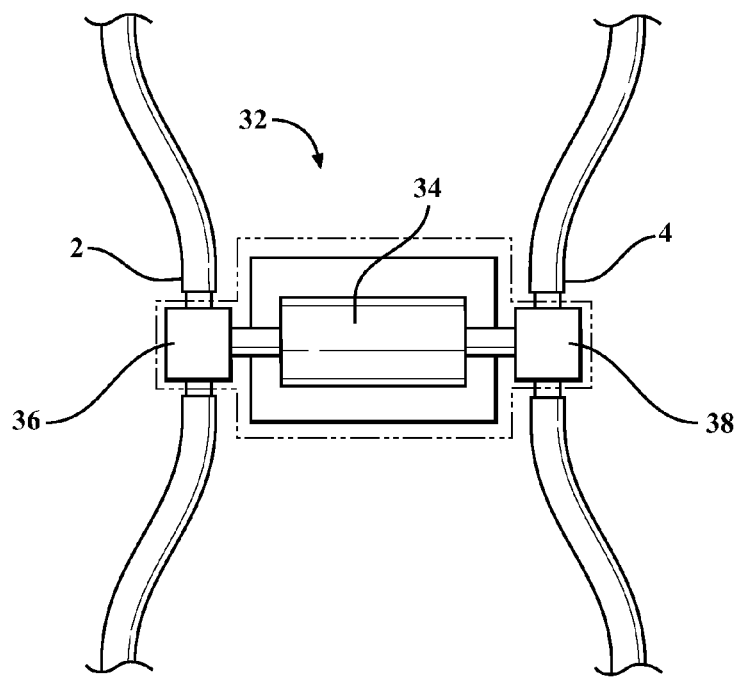
FIG. 3 is another variant schematic illustration of a fertility regulator using a single actuator to actuate both seminal valves. The actuator would be activated by means of an externally positioned hand-held controller for providing an electromagnetic generating input (or like form of wireless energy transfer) to cause opening/closing of the actuator component.

Referring now to FIG. 3, illustrated is generally depicted at 32 a schematic illustration of a variation of fertility regulator in comparison to that depicted in FIG. 1. This variant has a single actuator 34 incorporating one or a pair of valves 36 and 38 of any desired type (including without limitation any of a ball, clamp, globe, flow, butterfly, puppet, spool, gate, control or the like). The actuator is again provided in combination with the externally positioned hand-held controller (FIG. 11) for providing an electromagnetic generating input to cause opening/closing of the actuator component.

Figure 4A:
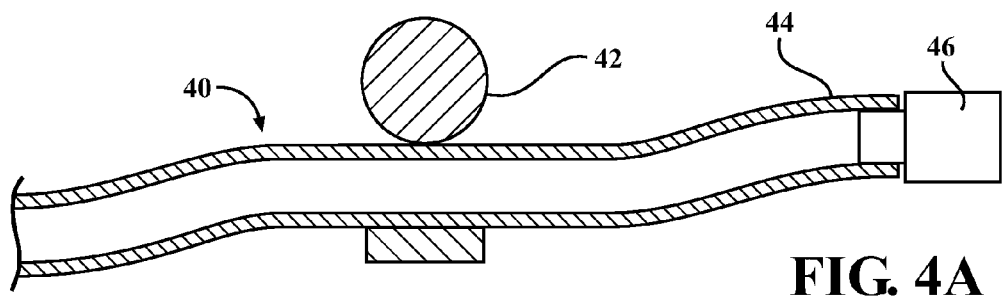
FIGS. 4A and 4B illustrate a clamp open/closed scheme incorporated into one further variant of the invention.
Figure 4B:
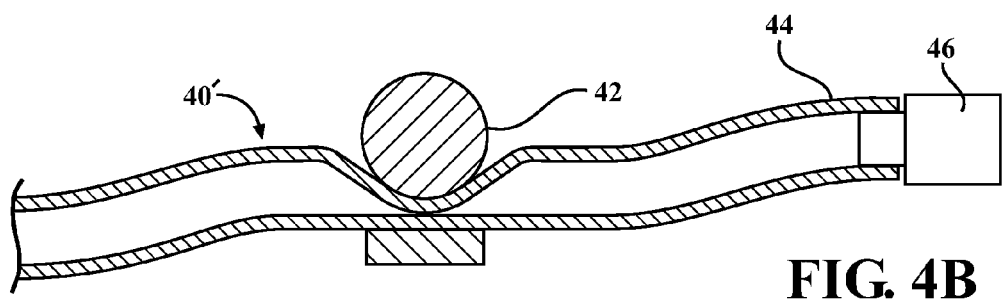

Proceeding to FIG. 4, FIGS. 4A and 4B, illustrated are a pair of succeeding illustrations of a clamp open/closed scheme, generally at 40, incorporated into one further variant of the invention. FIG. 4A illustrates a displaceable clamping arm 42 (shown in section form as a circle), such as which is constructed of an electromagnetic responsive metal, and which is in a first non-interfering position relative to a spliced bypass portion 44 communicated with a selected vas deferens tube (via nipple 46 which in turn connects a previously sectioned end of the vas deferens tube not shown). FIG. 4B successively illustrates, at 40', the clamping arm 42 in a collapsing/pinching configuration and in which seminal flow through the spliced location 44 is interrupted.

Figure 5:
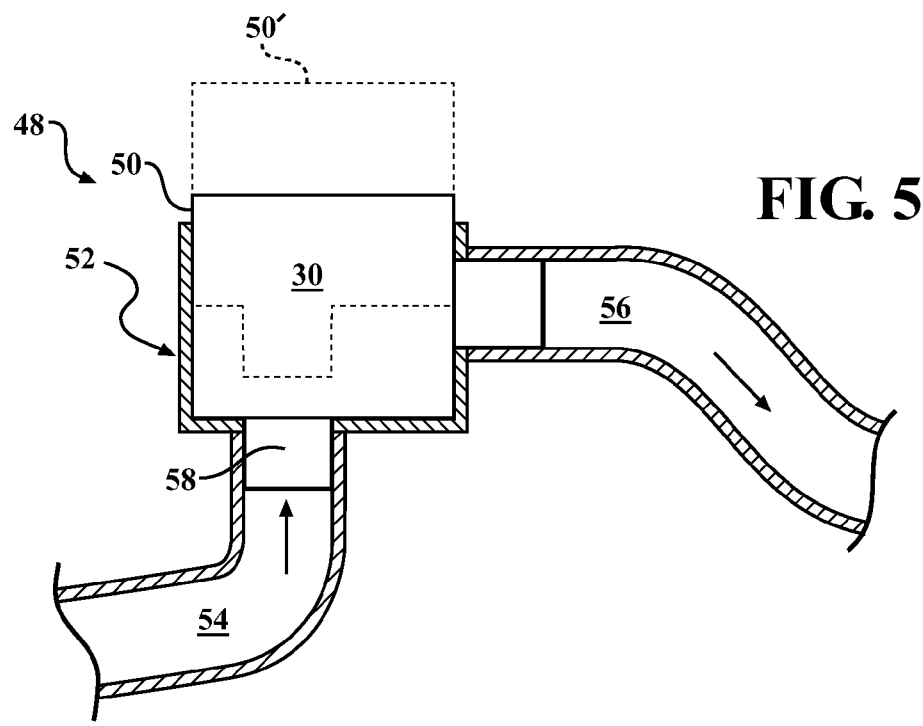
FIG. 5 is a further illustration of a globe valve configuration.

FIG. 5 is a further illustration generally shown at 48 of a globe valve 50 arranged so as to seat within a location 52 established in interrupting fashion within a bypass splice configuration to which are communicated inlet 54 and outlet 56 portions, these again being connected in spliced fashion with a selected reproductive ducts (e.g., vas deferens). As shown, the location 52 is illustrated as a seat for receiving the valve in displaceable fashion and such that a projecting portion 58 of the globe valve 50 is displaced between a first position in which is seals the inlet 54 to a second and upwardly displaced position (in phantom at 50') in which the valve is upwardly displaced a sufficient distance to permit seminal flow from the inlet 54 to outlet 56. As with the embodiments previously described, the valve 50 can be constructed of an electromagnetic responsive element so as to be actuated by the externally positioned controller in the manner previously described.

Figure 6:
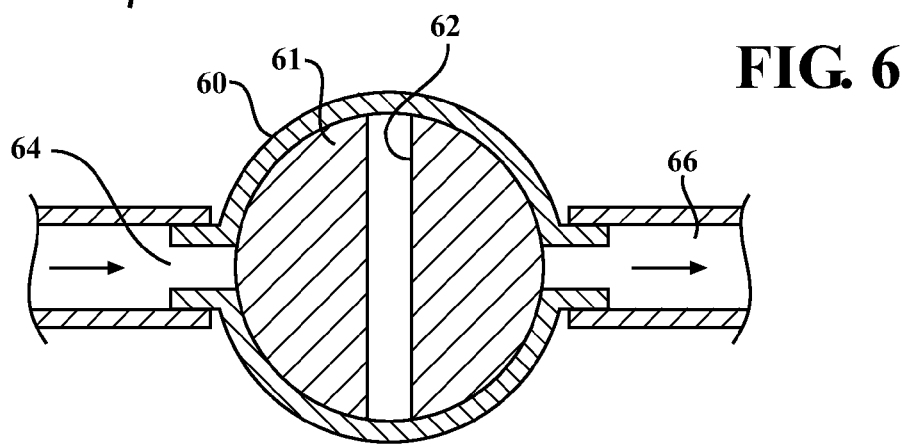
FIG. 6 is an illustration of a rotating ball valve configuration.

FIG. 6 is an illustration in cutaway of a rotating ball valve configuration exhibiting a fixed and spherical shaped housing 60 including inlet and outlet nipple ends and within which is disposed a spherical shaped valve element 61 exhibiting a central through passageway (see inner wall 62) according to a further desired embodiment. As with previous embodiments, the spherical element 61 is metallic in construction and, depending upon the electromagnetic induced rotating motion imparted, selectively opens or closes a bypass condition depicted by inlet 64 and outlet 66.

As with each of the disclosed embodiments herein, it is envisioned that the construction of the actuator/valve element is such that an electrical signal (e.g., DC or AC generated) input originating from the external hand-held controller causes the actuating element to shift, rotate, pivot, angle or translate in any desired direction or trajectory in order to selectively permit or interrupt seminal flow. The construction of the outer fixed housing 60 is further such that it can incorporate electromagnetic receiver circuitry or other material composition to facilitate actuation of the element 60.

FIGS. 7A and 7B illustrate closed and open positions, respectively at 68 and 70, of an angled gate valve configuration. Consistent with the earlier description, a piston 72 or other AC coil induced and electro-magnetic responsive and driving component is both supported by and actuated relative to a fixed housing 74 positioned in communication with a bypass or implanted portion 76 to which is connected the vas deferens or fallopian tube. An end supported and combined linearly displaceable and pivotal gate portion 78 is selectively displaced between flow closed (FIG. 7A) and flow open (FIG. 7B) positions.

FIG. 8 is again an environmental illustration of one version of a vas deferens implant 80 mounted in accordance with the male implantable version of the present invention. Bypass components 82 and 84 of the implant 80 each include a pair of spliced locations 86 and 88 connecting to locations of the vas deferens 2 and 4. Similarly, FIG. 9 is an illustration generally at 90 of a regulator device and which illustrates a pair of identical implantable components each shown at 92. Without elaboration, each of the regulator devices 92 are of a construction similar to that as previously described, with the exception that each is incorporated into either of the female reproductive ducts (also again known as fallopian tubes and depicted at 6 and 8).

Figure 10A:
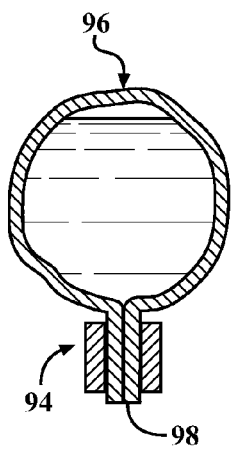
FIGS. 10A-10C illustrate a tubal bladder control assistance device which creates constriction around the urethra assisting the sphincter in preventing the bladder from premature release of stored urine and which further discloses a manual release feature provided by a hand held device for emptying at a desired time.
Figure 10B:
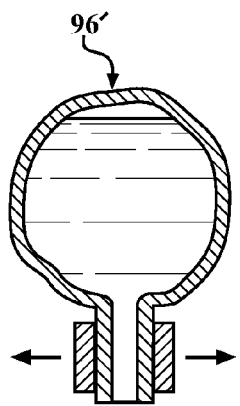
Figure 10C:
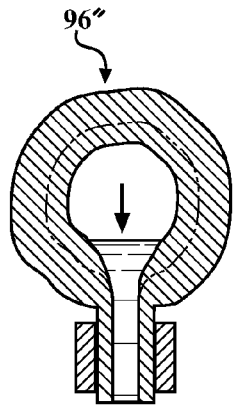

Finally, and referring to each of FIGS. 10A-10C in succession, illustrated is a tubal bladder control assistance device 94 unrelated to the disclosure of FIGS. 1-9 according to a further embodiment and which creates a selective constriction around a patient's urethra 96, thereby assisting sphincter 98 in preventing the bladder from premature release of stored urine. A manual release feature is further provided by a hand held device (shown in FIG. 11) for actuating the device (as further depicted successively at 96' and 96" in FIGS. 10B and 10C respectively) to permit emptying of the bladder contents at any desired time or when urged by the body's detrusor which sends a signal to the brain telling you that it is time to urinate.

Having described my invention, other and additional preferred embodiments will become apparent to those skilled in the art to which it pertains, and without deviating from the scope of the appended claims. In particular, the invention can also be configured for use in veterinary sciences and such as to allow for selective timing of animal (including cattle and other purebred applications) fertility such as for purposes of targeting breeding cycles or the like.

I claim:

1. An on/off fertility regulator device, comprising:
   an implantable housing incorporating at least one actuator;
   a pair of opposite extending valves operable by a pair of extending valve actuators for respectively engaging first and second reproductive ducts and which is adapted to being mounted between interrupted conduit locations associated with the reproductive ducts extending within a body cavity of a user, the conduit locations being reattached to inter-fitting nipple portions associated with said valve in order to fluidly communicate the conduit locations;
   an electro-magnetic inducing component incorporated within housing for powering a displaceable portion of said actuator extending to an open/close element located within valve and to establish an open position for permitting flow through the duct and a closed position for interrupting flow through the duct; and
   a separate handheld controller positioned in external proximity to the implanted actuator, said controller incorporating wireless energy transfer circuitry for energizing said electro-magnetic inducing component and causing movement of said valve between said flow permitting and interrupting positions.

2. The device as described in claim 1, further comprising said controller having a specified shape and size and generating at least one of an DC or an AC electromagnetic inducing signal.

3. The device as described in claim 2, further comprising said implant having a body incorporating receiver circuitry and which is configured to receive said signal from said controller.

4. The device as described in claim 1, a pair of nipples extending from first and second locations of said implant for receiving the spliced ends of the reproductive duct.

5. The device as described in claim 4, further comprising a conduit ribbon extending from said implant and which can communicate at least one of an AC or DC generated electromagnetic input in order to actuate said valve actuator.

\* \* \* \* \*